United States Patent [19]

Tuneberg

[11] Patent Number: 5,067,897
[45] Date of Patent: Nov. 26, 1991

[54] TWIN TIE WING BRACKET

[75] Inventor: Lee H. Tuneberg, Sheboygan, Wis.

[73] Assignee: American Orthodontics Corporation, Sheboygan, Wis.

[21] Appl. No.: 513,607

[22] Filed: Apr. 24, 1990

[51] Int. Cl.$^5$ .............................................. A61C 3/00
[52] U.S. Cl. ......................................... 433/8; 433/10
[58] Field of Search .................................... 433/8, 9, 10

[56] References Cited

U.S. PATENT DOCUMENTS

| | | | |
|---|---|---|---|
| D. 290,040 | 5/1987 | Kelly | D24/16 |
| 3,626,593 | 12/1971 | Ridgeway | 32/14 A |
| 3,765,091 | 10/1973 | Northcutt | 433/9 |
| 3,922,787 | 12/1975 | Fischer et al. | 433/8 X |
| 4,415,330 | 11/1983 | Daisley et al. | 433/8 X |
| 4,487,580 | 12/1984 | Ridgeway | 433/3 |
| 4,531,911 | 7/1985 | Creekmore | 433/9 X |
| 4,659,309 | 4/1987 | Merkel | 433/9 |
| 4,842,512 | 6/1989 | Kesling | 433/8 |
| 4,859,179 | 8/1989 | Kesling | 433/8 |
| 4,877,398 | 10/1989 | Kesling | 433/8 |

Primary Examiner—Robert P. Swiatek
Assistant Examiner—Nicholas D. Lucchesi
Attorney, Agent, or Firm—Lloyd L. Zickert

[57] ABSTRACT

A twin tie wing orthodontic bracket having a pair of substantially parallel spaced tie wings extending from a base portion adapted to be attached to a tooth, and a horizontally opening buccolabially extending archwire slot and cutouts at the mesial and distal sides of the bracket at the archwire slot and the buccolabial face which increases the interbracket distance and thereby increases the range of the archwire and decreases the force the archwire exerts on the brackets.

18 Claims, 2 Drawing Sheets

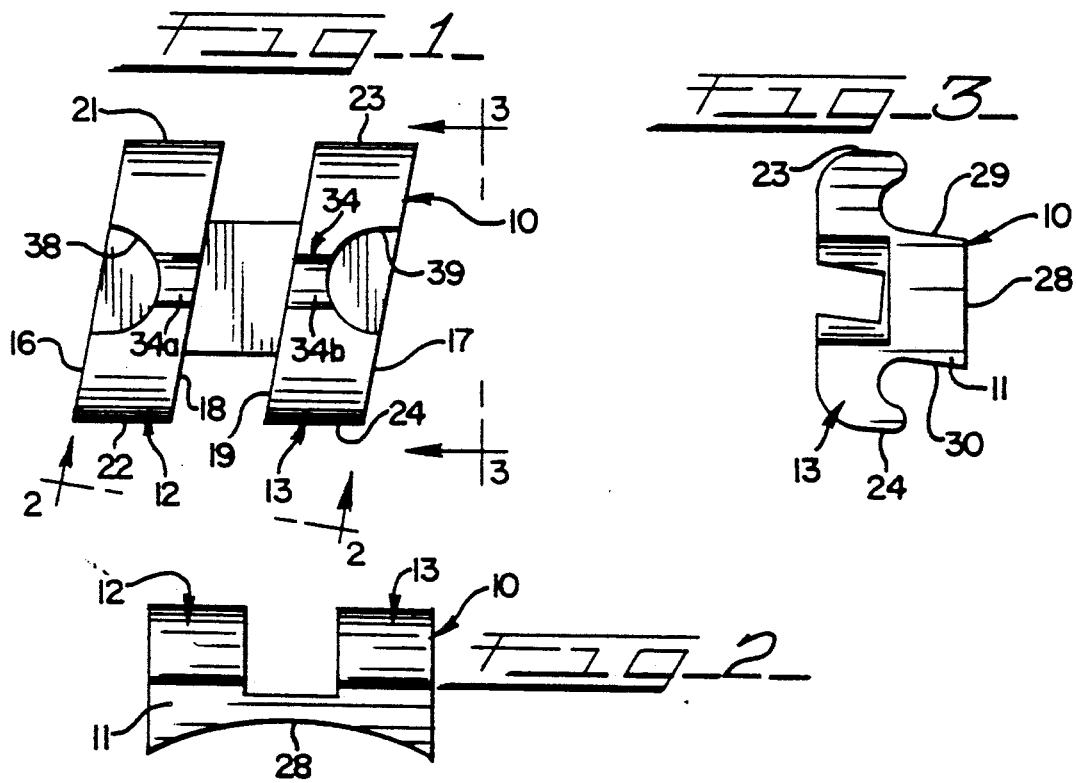

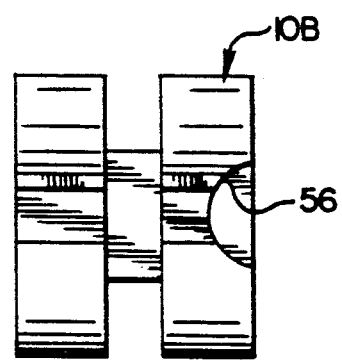
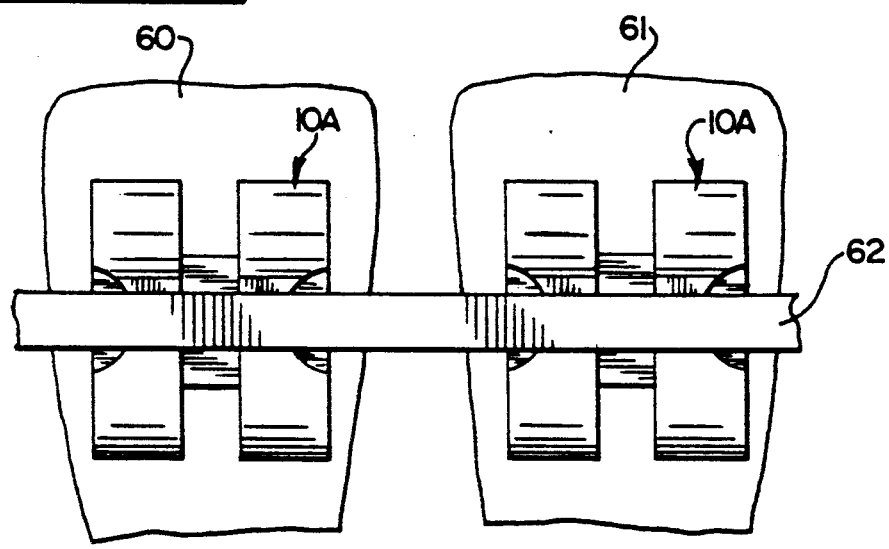
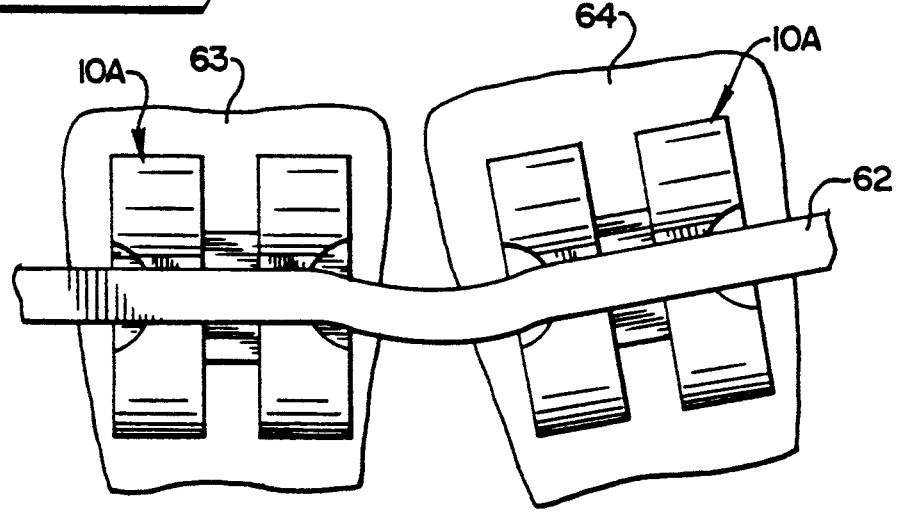

TWIN TIE WING BRACKET

DESCRIPTION

This invention relates in general to an orthodontic bracket, and more particularly to a twin tie wing orthodontic bracket having a horizontally opening and buccolabially extending archwire slot, and still more particularly to a twin tie wing bracket having mesial and distal cutouts in the buccolabial face at the archwire slot to increase the interbracket distance for increasing the range of the archwire and decreasing the forces exerted by the archwire on the brackets.

BACKGROUND OF THE INVENTION

Heretofore, it has been well known to provide a twin tie wing bracket having two distinctly separate tie wings with an archwire slot that is horizontally opening and buccolabially extending for use in the well known edgewise technique of orthodontic treatment. It has also been known to form such a bracket such that it has a buccolingual rhomboidal profile and also a buccolabial rhomboidal profile so that the archwire slot is squared with both profiles. Such a bracket is shown in U.S. Pat. No. 4,659,309.

It has also been well known to provide a single wing bracket having deep mesial and distal cutouts at the archwire slot for purposes of allowing unlimited tipping and uprighting movements in an edgewise bracket such as the bracket long ago developed by Alexander Sved, as disclosed in column 2 of U.S. Pat. No. 4,842,512.

Another form of a single tie wing edgewise bracket is shown in U.S. Design Pat. No. 290,040, which while having the appearance of a twin tie wing bracket and which does include cutouts at the mesial and distal sides of the bracket along the archwire slot, is in fact nothing more than a single wing bracket having four tie wing tips extending from the bracket slot that is positioned intermediate the tie wings, and thus cannot provide the advantages of a twin-wing bracket.

It has also been known to provide a twin tie wing bracket where the mesial and distal sides of the bracket are arcuately formed such as illustrated in U.S. Pat. No. 4,487,580 for the purpose of facilitating the gripping by an instrument. A bracket of this type is marketed under the trademark "Edgeway" by Ortho Organizers.

It has also been known to provide a single tie wing bracket having wings that are tapered to guide a tensioned resilient ligature into a seated position relative to the central portion, as illustrated in U.S. Pat. No. 3,626,593.

The prior known brackets and those above identified are limited in their operation and function.

It is well known that a twin tie wing bracket has many advantages over a single tie wing bracket. Twin tie wing brackets, sometimes called a twin bracket or a siamese bracket, by increasing mesiodistal archwire engagement, maintain better rotational control. Secondly, a true twin bracket allows effective single wing ligation on severely rotated teeth so that better leverage can be obtained. The true twin bracket further allows use of auxiliary components which are helpful with very short mesiodistal slot lengths. Such auxiliary components include torquing auxiliaries which can be used because they are disposed between the tie wings. Twin ligature ties may be used, one on each tie wing. Further, the mesiodistal slot length is increased over a single width bracket to yield more effective tip control.

Particularly, with respect to the bracket of U.S. Design Pat. No. 290,040, which is not a true twin bracket, it is not possible to allow placement of the single ligature tie on a severely rotated tooth, as it would cause the archwire to be in empty space at the edge of the bracket which would not provide any control between the archwire and the bracket. Further, this configuration would not allow the use of auxiliaries to be placed under the archwire and in between the bracket base and the lingual of the archwire.

SUMMARY OF THE INVENTION

The twin tie wing bracket of the present invention differs from the standard twin tie wing bracket heretofore well known in that the tie wings are spaced closer together and cutouts are provided at the mesial and distal ends of the archwire slot so as to increase the interbracket distance that increases the range of the archwire, thereby decreasing the forces applied by the archwire to the brackets. It has been well known that tooth movements are faster with lighter forces as have been used in the Begg technique. Lighter forces are more comfortable to the patients and thereby enhance patient cooperation. Reduction of the wire force reduces the physiological tooth-moving force, which collectively speeds up treatment while greatly enhancing patient comfort and cooperation.

With the increased interbracket distance of the present invention over traditional twin brackets, the working wire distance of the archwire is increased, allowing the wire to more easily flex. The archwires used today have exceptional memory characteristics and tend to drag the teeth with the wire when it has a greater working wire distance by increasing the range of the archwire between the brackets and decreasing the forces to the teeth. It will be appreciated that this is achieved by reducing the constraining action by the brackets on the wire extending between brackets. Because of the shortened overall slot length, ample tip allowance can still be provided.

While the "Edgeway" bracket generally illustrated in U.S. Pat. No. 4,487,580 appears to reduce the interbracket distance and, in fact, does somewhat reduce the interbracket distance, this bracket is not formed for purposes of reducing the interbracket distance. The opposed mesial and distal edges are full-sized twin, and the concave mesial and distal sides define sharp tie-wing corner edges that are irritating to the patient. When the patient complains and rounding or reducing of the acute angle at the tie wing edges is accomplished by a suitable instrument, then the undertie area is reduced, which results in ligature loss or difficulty in tying.

The bracket of the present invention significantly increases the interbracket distance in order to provide the proper increase in range of archwire movement. The overall mesiodistal dimension of an "Edgeway" bracket is decreased only by an average of fifteen percent compared to at least a forty percent decrease in the overall mesiodistal dimension of the bracket of the present invention.

Accordingly, the present invention is unique in that it is structured to enhance orthodontic treatment where the length of treatment time can be reduced while the comfort level of the patient is at the same time materially improved, thereby resulting in significantly better end results.

It is therefore an object of the present invention to provide a new and improved twin tie wing bracket which increases the interbracket distance to materially increase the working range of the archwire while materially reducing the archwire forces.

Another object of the present invention is in the provision of a new and improved twin tie wing bracket having a full size tie wing width on a compact scale with a materially shortened archwire slot to increase interbracket distance and decrease the wire forces so as to provide a system that is more physiologically healthy to the periodontium and the bony structure of the mouth.

A still further object of the present invention is in the provision of a true tie wing bracket having all the features of a twin tie wing bracket while being formed with recesses at the ends of the archwire slot in order to shorten the archwire slot and materially increase the range of the archwire, thereby decreasing the archwire forces applied to the brackets and materially enhancing orthodontic treatment.

Other objects, features and advantages of the invention will be apparent from the following detailed disclosure, taken in conjunction with the accompanying sheets of drawings, wherein like reference numerals refer to like parts.

DESCRIPTION OF THE DRAWINGS

FIG. 1 is a front or buccolabial view of the bracket of the invention for a central;

FIG. 2 is a bottom plan view of the bracket of FIG. 1 taken substantially along line 2—2 thereof and looking in the direction of the arrows;

FIG. 3 is a side elevational view of the bracket of FIG. 1 taken substantially along line 3—3 thereof and looking in the direction of the arrows;

FIG. 4 is a front or buccolabial view of a bracket according to the invention which is designed for a lower anterior tooth;

FIG. 5 is a bottom plan view of the bracket of FIG. 4;

FIG. 6 is a side elevational view of the bracket of FIG. 4 taken generally along line 6—6 of FIG. 4 and looking in the direction of the arrows;

FIG. 7 is a front or buccolabial view of a modified bracket where a cutout is provided only on one side;

FIG. 8 is a front or buccolabial view of two brackets of the type shown in FIGS. 4 to 6 mounted on adjacent teeth with an archwire fitted in the archwire slots of the bracket and where ligatures are omitted for purposes of clarity; and FIG. 9 is a view similar to FIG. 8 except that one of the teeth is angularly disposed to the other so as to illustrate the bend in the archwire portion extending between the brackets and where ligatures have been omitted for purposes of clarity.

DESCRIPTION OF THE INVENTION

Referring now to the drawings and particularly to the embodiment of FIGS. 1 to 3, one form of the bracket of the present invention is illustrated and generally identified by the numeral 10. This bracket includes a base or base portion 11 and a pair of parallel spaced apart tie wings 12 and 13. The tie wings are in substantially parallel relation and include mesial and distal sides. Whether a side is mesial or distal will depend upon whether it is used in the right or left-hand side of the mouth. Bracket 10 is for an upper left central, it being appreciated that the top of the bracket as viewed in FIG. 1 would be gingivally positioned. The bracket of the invention in FIGS. 4 to 6 is designed for use on the lower anterior.

Since bracket 10 is for an upper left central, the mesial side is indicated by the numeral 16 and the distal side by the numeral 17, it also being appreciated that the mesial side of tie wing 12 is also the same as the mesial side 16 of the bracket and the distal side of the tie wing 13 is the same as the distal side 17 of the bracket. The distal side of tie wing 12 is indicated at 18, while the mesial side of the tie wing 13 is indicated at 19. The mesial and distal sides of the tie wings are substantially parallel to each other as are the mesial sides 16 of the bracket and the distal sides 17 of the bracket. Similarly, the ends of the tie wing tips are substantially parallel to each other. Tie wing 12 includes a gingival edge 21 on the upper tie wing tip and an occlusal edge 22 on the lower tie wing tip. Similarly, tie wing 13 includes a gingival edge 23 on the upper tie wing tip and an occlusal edge 24 on the lower tie wing tip.

The base portion 11 includes an attachment face 28 which may be concave as illustrated in FIG. 2 for purposes of facilitating the fit on a tooth or on a bonding pad. If the tooth is made of ceramic material, the use of a bonding pad is not needed as the bracket is then directly bonded to a tooth. However, if the bracket is metal, it usually will be suitably attached to a bonding pad, which is in turn bonded to a tooth. The gingival side 29 and the occlusal side 30 of the base portion 11, together with the gingival and occlusal ends of the tie wing tips, are generally rhomboidal in profile, it being appreciated that such is not necessary in order to embrace the present invention.

It should be further appreciated that the front profile of the bracket is also rhomboidal, as is preferable for a central, and certain teeth, but the present invention is applicable on brackets that are not rhomboidal, as shown in FIGS. 4 to 6. Further, it should be appreciated that while the mesial and distal sides of the bracket, as well as the gingival and occlusal edges of the tie wings, are illustrated as being parallel, these surfaces may be rounded and still function as generally parallel in relation to each other.

Thus, the bracket may be directly attached to a tooth if it is ceramic or plastic, but indirectly attached to a tooth through a bonding pad if it is of metal and a bonding pad is desired.

A horizontally opening and buccolabially extending archwire slot 34 is provided in the bracket and which includes a segment 34a in the tie wing 12 and a segment 34b in the tie wing 13. It will be appreciated that the segments are aligned with each other and coact to form a single archwire slot for receiving an archwire. The archwire slot is rectangular in form as the bracket is one of the edgewise type for principally practicing the edgewise technique. In this respect, a rectangular wire may be received in and fill the archwire slot and be suitably ligated to the bracket. Of course, a round wire could be used if desired. Whether it is ligated to one or both of the tie wings, metal or elastic ligatures may be used. The bracket of the present invention is unique in that the length of the archwire slot is decreased by providing cutouts at opposite ends of the archwire slot including the cutout 38 at the mesial side of the bracket in the tie wing 12 and the cutout 39 at the distal side of the bracket in, the tie wing 13. The cutouts shorten the length of the archwire slot 34 while serving to materially increase the interbracket distance between brackets on adjacent teeth. By increasing the interbracket distance, the working range of the archwire between the brackets is greatly increased and the forces applied by the archwire are also decreased. A decrease in the forces ultimately results in speeding up the tooth movement while aiding patient comfort and making it less painful for a patient to undergo orthodontic treatment. The cutouts are sized to allow working room for the wire before it is constrained by the slot. Sufficient open area must be provided to allow such flexing as to increase the interbracket distance.

The cutouts decrease the overall mesiodistal archwire slot dimension to at least thirty percent and preferably at least forty percent. With respect to the dimensions of the bracket of FIG. 1, the width of the tie wings would be 0.050 inches, while the distance between the tie wings would be 0.040 inches, and the depth of the cutouts from the mesial or distal edges inwardly would be 0.030 inches. This significant decrease in the overall length of the archwire slot significantly increases the interbracket distance to materially increase the working range of the archwire between brackets and decrease the forces induced by the archwire and transmitted to the brackets.

As noted in FIG. 1, the upper and lower sides of the archwire slot 34 are parallel to the gingival and occlusal edges of the bracket. Similarly, the upper and lower sides of the archwire slot as viewed in FIG. 3 are parallel to the upper and lower sides of the base portion and the overall configuration of the bracket.

Referring now the embodiment of FIGS. 4 to 6, the bracket is generally identified by the numeral 10A and includes a base portion 50 and tie wings 51 and 52. This bracket is designed for use on a lower anterior and is therefore rectangular in front profile and side profile, as seen in FIGS. 4 and 6. The upper edge as illustrated would be toward the occlusal. The base portion has an attachment face 53 and an archwire slot 54 which is of the same type as the archwire slot in FIG. 1. The opposite ends of the archwire slot are cut out at 55 and 56 in order to reduce the length of the archwire slot and to increase the working range of the archwire between brackets in the same fashion as in the embodiment of FIGS. 1 to 3.

It will also be appreciated that other brackets designed for other teeth will be dimensioned accordingly. For example, the bracket designed for the upper laterals would also be rhomboidal in profile, both front and side, but would be of a smaller width than the bracket used for the centrals which is that one shown in FIGS. 1 to 3. Again, cutouts would be provided at the ends of the archwire slot in order to materially increase the interbracket distance and increase the working range of the archwire.

In view of the foregoing, it can be appreciated that the bracket of the present invention is unique and that it increases the effectiveness of the bracket to enhance orthodontic treatment.

Additionally, it should be appreciated that while cutouts are shown on both sides of the bracket they may be provided on only one side of the bracket, as shown by the bracket 10B in FIG. 7, if it is not necessary or desirable to increase the working range of the archwire at the other side of the bracket. Further, such a bracket may be used in a system where the other brackets are of the standard configuration with no cutouts or in a system where only the immediately adjacent bracket on the side of the bracket having a cutout would likewise have a cutout.

Reference is made to FIG. 8 which illustrates brackets of the invention on adjacent teeth with an archwire fitted in the brackets. Ligatures have been omitted for purposes of clarity, but it will be understood that ligatures of a suitable type will be used in order to retain archwire in the archwire slots of the brackets. The brackets are mounted on adjacent teeth 60 and 61, which are in alignment so that archwire 62 appears straight when fitted in the brackets. Nevertheless, it can be appreciated that the interbracket distance is increased by use of the cutouts as the archwire is not constrained by the archwire slots at the adjacent edges of the bracket. Rather, the archwire extends through the open areas of the cutouts such that flexing can take place between the entire portion of the archwire that is not in engagement with the archwire slots.

As seen in FIG. 9, the adjacent brackets 10A are mounted on teeth 63 and 64 where tooth 64 is angularly disposed from tooth 63. Because of the greater interbracket distance afforded by the cutouts of brackets 10A, it can be seen that the archwire 62 flexes in the cutouts. By being able to flex over a greater length of the archwire portion between the brackets, the forces produced by the archwire and imparted to the brackets is reduced. As above mentioned, the lower forces are more comfortable to the patient and also effect faster movement to shorten the overall time needed for orthodontic treatment.

Further, it should be appreciated that while the cutouts are illustrated as being semi-circular in shape, they could be rectangular or polygonal in shape or of any suitable shape in order to allow the archwire sufficient room to flex relative to the bracket to thereby increase the interbracket distance and increase the working range of the archwire.

It will be understood that modifications and variations may be effected without departing from the scope of the novel concepts of the present invention, but it is understood that this application is to be limited only by the scope of the appended claims.

The invention is hereby claimed as follows:

1. A twin tie-wing orthodontic bracket comprising a base having an attachment face for mounting on a tooth, said bracket having a front profile and a side profile, a pair of tie wings extending from the base, said tie wings being in substantially parallel relation, and a rectangular in form archwire slot extending through both tie wings and adapted to receive an archwire to control precise tooth position, said tie wings having upper and lower tie-wing tips of substantially the same size, and cutouts in the tie wings and the archwire slot at the opposite ends of the archwire slot at the buccolabial face of the bracket to increase the interbracket distance with a like bracket on an adjacent tooth such as to increase the range of an archwire in the archwire slots of the brackets and decrease the forces produced by the archwire.

2. The bracket of claim 1, wherein the cutouts are sized occlusogingivally to allow occlusogingival flexing of the archwire.

3. The bracket of claim 1, wherein the cutouts are semi-circular in shape as viewed from the front profile of the bracket.

4. The bracket of claim 1, wherein the front profile is rectangular.

5. The bracket of claim 1, wherein the front profile is rhomboidal.

6. The bracket of claim 5, wherein the side profile is rhomboidal.

7. The bracket of claim 1, wherein the cutouts decrease the overall mesiodistal dimension of the archwire slot by at least thirty percent.

8. The bracket of claim 1, wherein the cutouts decrease the overall mesiodistal dimension of the archwire slot by at least forty percent.

9. A twin tie-wing orthodontic bracket for use with an archwire to impart corrective forces to a tooth comprising, a base portion for attachment to a tooth, a pair of tie wings extending from the base portion, said tie wings being in substantially parallel relation, a horizontally opening rectangular in form archwire slot extending through both tie wings and adapted to receive an archwire to control precise tooth position, the mesial and distal sides of the bracket being essentially parallel to each other, the occlusal and gingival sides of the tie wings being essentially parallel to each other, said tie wings having upper and lower tie wing tips of substantially the same size as measured from the archwire slot, and cutouts in the archwire slot at the mesial and distal sides of the tie wings and the buccolabial face of the bracket to substantially increase the interbracket distance in relation to a like bracket on an adjacent tooth so as to substantially increase the range of the archwire in the archwire slots of the adjacent brackets and decrease the forces produced by the archwire.

10. The bracket of claim 9, wherein the tie wings are substantially the same size.

11. The bracket of claim 9, wherein the cutouts substantially shorten the archwire slot to increase the movement range and decrease the forces of the archwire between adjacent brackets while otherwise maintaining the bracket for full use as a twin tie wing bracket.

12. The bracket of claim 9, wherein the cutouts decrease the overall mesiodistal dimension of the archwire slot by at least thirty percent.

13. The bracket of claim 9, wherein the cutouts decrease the overall mesiodistal dimension of the archwire slot by at least forty percent.

14. An orthodontic system for treating a patient including at least two twin tie-wing brackets on adjacent teeth interconnected by an archwire which imparts corrective forces to one or both teeth through the brackets, each bracket comprising a base portion for attachment to the tooth, a pair of tie wings extending from the base portion, said tie wings extending substantially parallel to each other and having substantially parallel mesial and distal sides, a horizontally opening rectangular in form archwire slot extending through said tie wings and adapted to receive an archwire to control precise tooth position, said tie wings having upper and lower tie wings of substantially the same size, and cutouts in the adjacent tie wings of said brackets and the archwire slot at the buccolabial face of each bracket, said cutouts being sized to substantially increase the interbracket distance between the brackets so as to increase the range of the archwire by increasing the length of the archwire between the brackets that is not constrained by the archwire slots of the brackets and decrease the forces produced by the archwire.

15. The system of claim 14, wherein the cutouts are on both sides of each bracket.

16. The system of claim 14, wherein the cutouts decrease the overall mesiodistal dimension of the archwire slot by at least thirty percent.

17. The system of claim 14, wherein the cutouts decrease the overall mesiodistal dimension of the archwire slot by at least forty percent.

18. A twin tie-wing orthodontic bracket comprising a base having an attachment face for mounting on a tooth, a pair of tie wings extending from the base, said tie wings being in substantially parallel relation, and a rectangular in form archwire slot extending through the tie wings and adapted to receive an archwire to control precise tooth position, said tie wings having upper and lower tie-wing tips of substantially the same size, and a cutout in the archwire slot at one end of the archwire slot and at the buccolabial face of the bracket to increase the interbracket distance with a bracket on an adjacent tooth such as to increase the range of an archwire in the archwire slots of the brackets and decrease the forces produced by the archwire.

* * * * *